(12) United States Patent
Turnbull et al.

(10) Patent No.: US 11,181,497 B2
(45) Date of Patent: Nov. 23, 2021

(54) SYSTEM AND METHODS FOR CHEMICAL DETECTION AND AMPLIFICATION

(71) Applicants: Gentex Corporation, Zeeland, MI (US); Vaporsens, Inc., Salt Lake City, UT (US)

(72) Inventors: Robert R. Turnbull, Holland, MI (US); Drew G. Janibagian, Salt Lake City, UT (US); T. Frank Delatorre, American Fork, UT (US); Ross A. Riches, Sandy, UT (US); Benjamin R. Bunes, Murray, UT (US)

(73) Assignees: GENTEX CORPORATION, Zeeland, MI (US); VAPORSENS INC, Salt Lake City, UT (US)

( * ) Notice: Subject to any disclaimer, the term of this patent is extended or adjusted under 35 U.S.C. 154(b) by 0 days.

(21) Appl. No.: 17/095,808

(22) Filed: Nov. 12, 2020

(65) Prior Publication Data
US 2021/0148844 A1    May 20, 2021

Related U.S. Application Data

(60) Provisional application No. 62/935,295, filed on Nov. 14, 2019.

(51) Int. Cl.
*G01N 27/12*     (2006.01)
*G01N 33/00*     (2006.01)
*G01N 15/06*     (2006.01)

(52) U.S. Cl.
CPC ........... *G01N 27/128* (2013.01); *G01N 15/06* (2013.01); *G01N 27/122* (2013.01); *G01N 33/0031* (2013.01); *G01N 2015/0693* (2013.01)

(58) Field of Classification Search
CPC .. G01N 27/122; G01N 27/12; G01N 33/0031; G01N 27/128; G01N 15/06
See application file for complete search history.

(56) References Cited

U.S. PATENT DOCUMENTS

| | | | |
|---|---|---|---|
| 4,847,783 A * | 7/1989 | Grace | G01N 27/123 702/24 |
| 5,725,425 A | 3/1998 | Rump et al. | |
| 6,225,910 B1 | 5/2001 | Kadwell et al. | |
| 6,326,897 B2 | 12/2001 | Kadwell et al. | |
| 6,653,942 B2 | 11/2003 | Kadwell et al. | |
| 6,876,305 B2 | 4/2005 | Kadwell et al. | |
| 6,936,828 B2 | 8/2005 | Saccomanno | |

(Continued)

FOREIGN PATENT DOCUMENTS

| | | |
|---|---|---|
| GB | 2193570 B | 1/1990 |
| JP | 2017116287 A | 6/2017 |

*Primary Examiner* — Paul M. West
(74) *Attorney, Agent, or Firm* — Price Heneveld LLP; Brian James Brewer

(57) ABSTRACT

A detection system includes at least one sensor configured to measure a presence of airborne particles and at least one amplifier circuit in communication with the at least one sensor. The amplifier circuit is configured to monitor a charge generated by the at least one sensor over a time interval. The system further includes a controller configured to monitor the charge accumulated in the at least one amplifier circuit from the at least one sensor at the time interval. In response to the charge of the at least one amplifier circuit, the controller detects the presence of the airborne particles.

18 Claims, 7 Drawing Sheets

(56) References Cited

U.S. PATENT DOCUMENTS

| | | |
|---|---|---|
| 8,427,641 B2 | 4/2013 | Babico et al. |
| 8,452,489 B2 | 5/2013 | Marra |
| 2004/0063154 A1* | 4/2004 | Booth .................. G08B 17/113 |
| | | 435/7.1 |
| 2019/0323979 A1* | 10/2019 | Cammenga .......... G01N 27/126 |

* cited by examiner

SYSTEM AND METHODS FOR CHEMICAL DETECTION AND AMPLIFICATION

CROSS-REFERENCE TO RELATED APPLICATIONS

This application claims priority under 35 U.S.C. § 119(e) and the benefit of U.S. Provisional Application No. 62/935,295 entitled SYSTEM AND METHODS FOR NANOFIBER DETECTION SENSOR AND AMPLIFIER CIRCUIT, filed on Nov. 14, 2019, by Robert R. Turnbull, the entire disclosure of which is incorporated herein by reference.

TECHNOLOGICAL FIELD

The present invention generally relates to a chemical detection system and, more particularly, to a monitoring circuit configured to detect a chemical presence.

BACKGROUND OF THE INVENTION

Identification and detection of materials may be beneficial in a variety of settings. The disclosure provides for a vapor and particulate sensor system that may be utilized to detect airborne chemical compositions for various applications.

SUMMARY

According to one aspect of the present disclosure, a detection system is disclosed. The system comprises at least one sensor configured to measure a presence of airborne particles and at least one amplifier circuit in communication with the at least one sensor. The amplifier circuit is configured to monitor a charge generated by the at least one sensor over a time interval. The system further comprises a controller configured to monitor the charge accumulated in the at least one amplifier circuit from the at least one sensor at the time interval. In response to the charge of the at least one amplifier circuit, the controller detects the presence of the airborne particles.

According to another aspect of the disclosure, a method for detecting a presence of airborne particles is disclosed. The method comprises supplying a plurality of bias voltages to a plurality of chemical sensors. The method further comprises receiving and accumulating current from each of the chemical sensors with a corresponding amplifier circuit and monitoring charges accumulated in the amplifier circuits from each of the chemical sensors over a plurality of corresponding accumulation periods. The method further comprises determining the resistance of each of the chemical sensors based on the charge of the amplifier circuits and voltage values of the plurality of bias voltages. The presence of the airborne particles is determined based on the resistances or conductance values determined for the chemical sensors.

According to yet another aspect of the disclosure, a chemical detection system comprising a plurality of chemical sensors configured to vary in resistance in response to a presence of airborne particles and a bias circuit configured to supply bias voltages to each of the chemical sensors. The system further comprises a plurality of amplifier circuits in communication with the chemical sensors and a controller. The controller is configured to control the bias circuit to supply the plurality of bias voltages to each of the plurality of chemical sensors and monitor charges accumulated in the amplifier circuits from the chemical sensors over the corresponding integration period in response to the bias voltages. The controller is further configured to determine the resistance of the chemical sensors based on the charges accumulated in the amplifier circuits and voltage values of the plurality of bias voltages and detect a chemical composition of the airborne particles based on the determined resistances of the chemical sensors.

These and other aspects, objects, and features of the present disclosure will be understood and appreciated by those skilled in the art upon studying the following specification, claims, and appended drawings. It will also be understood that features of each example disclosed herein may be used in conjunction with, or as a replacement for, features of the other examples.

BRIEF DESCRIPTION OF THE DRAWINGS

The following is a description of the figures and the accompanying drawings. The figures are not necessarily to scale, and certain features and certain views of the figures may be shown exaggerated in scale or in schematic in the interest of clarity.

In the drawings.

DETAILED DESCRIPTION OF THE PREFERRED EMBODIMENTS

Figure 1:
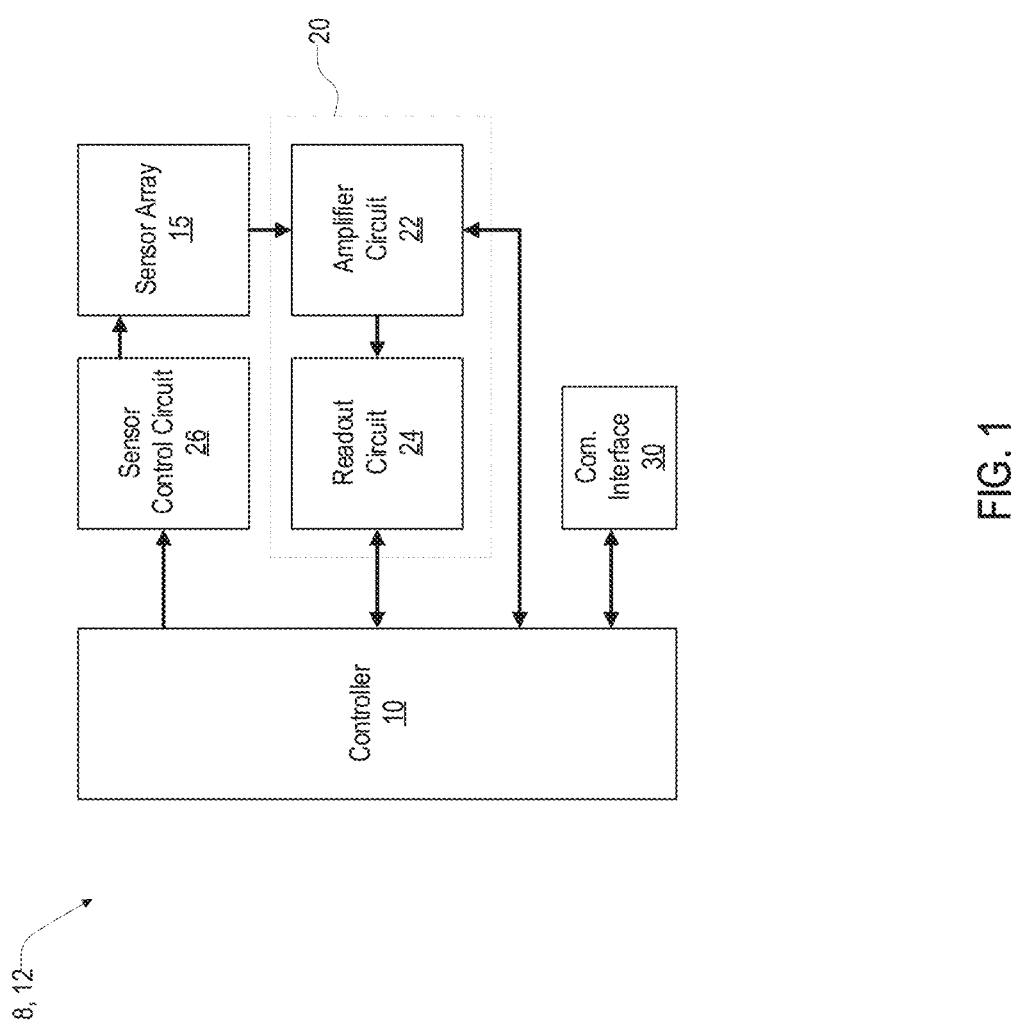
FIG. 1 is a block diagram of a chemical detection system comprising a chemical detection sensor.

It is to be understood that the specific devices and processes illustrated in the attached drawings and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise. As used herein, the term "and/or," when used in a list of two or more items, means that any of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination.

In this document, relational terms, such as first and second, top and bottom, and the like, are used solely to distinguish one entity or action from another entity or action, without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

Referring now to FIGS. 1-5, the disclosure provides for a detection system 8 configured to detect a variety of airborne chemical compounds or other measurable conditions. In various implementations, the system 8 may comprise a controller 10 configured to monitor and control a chemical detection device 12. The chemical detection device 12 is designed to identify a type and/or concentration of various chemicals based on signals communicated from at least one sensor 14 or a plurality of sensors 14 in an array 15. In various implementations, the at least one sensor 14 may be incorporated in a modular housing 16 forming the detection device 12. Accordingly, the disclosure provides for a chemical detection system 8 that may be flexibly applied in a variety of environments to detect one or more chemicals as provided by the following description.

Depending on the application of the system 8, each of the sensors 14a, 14b, 14c, etc. may be configured to detect specific chemicals or compounds that may be present in the environment local to the array 15. Similarly, signals from two or more of the sensors 14 in combination may be interpreted by the system 8 to identify the presence of a chemical or combination of chemicals. Such a detection may be inferred by the controller 10 based on an identifying signature or a combination of signals from the sensors 14 that are detected in response to and are representative of the presence of one or more chemicals or compounds. In this way, the system 8 may be scaled or tailored to suit a desired application based on the characteristics of each of the sensors 14. Accordingly, the system 8 may be configured to detect the presence of a variety of chemicals proximate to the array 15.

The signals output from the sensors 14 may comprise subtle changes in current. Such small changes, when considered in combination with signal noise and fluctuations that may occur over time, may result in the signals having transient variations that may cause issues identifying the status of the sensors 14. Accordingly, to accurately identify the presence of the chemicals, the system 8 may comprise a monitor circuit 20 configured to detect and communicate information that may be analyzed by the controller 10 to determine the resistance of each of the sensors 14a, 14b, 14c, etc. and to infer the chemicals present based on the resistance.

To effectively measure changes in the chemical composition of the environment proximate to the array 15, the monitor circuit 20 may be highly sensitive while also being capable of filtering noise related to transient variations output from each of the sensors 14a, 14b, 14c, etc. Accordingly, the monitor circuit 20 may comprise an amplifier circuit 22 configured to filter and track the changes in the current output from each of the sensors 14a, 14b, 14c, etc. over an integration period. The integration period may correspond to a monitoring interval over which the current output from each of the sensors 14a, 14b, 14c, etc. is accumulated. In response to a duration of the integration period for each of the sensors 14a, 14b, 14c, etc. expiring, the controller 10 may be configured to activate a readout circuit 24 (e.g. an analog-to-digital converter [ADC]) to read or convert the charges accumulated on the amplifier circuit 22 to digital values. Such values may then be reported by the controller 10 and/or stored, such that variations in the resistance of each of the sensors 14a, 14b, 14b, etc. of the array 15 may be calculated. Further detailed discussion of the sensor array 15 and the monitor circuit is provided in reference to FIG. 4.

Figure 4A:
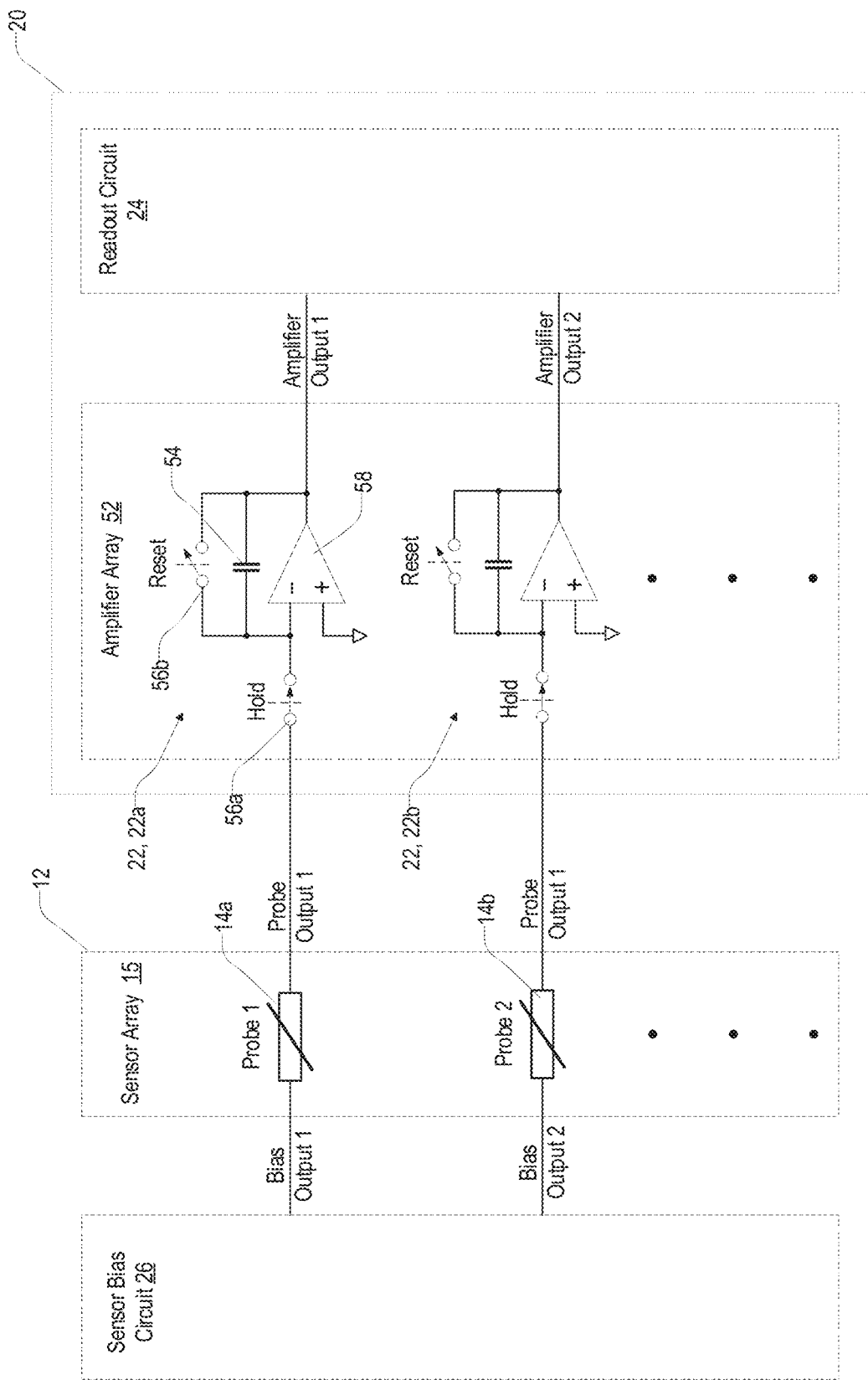
FIG. 4A is a schematic diagram of a chemical sensor array comprising a readout circuit configured to monitor voltage accumulated over an integration period.
Figure 4B:
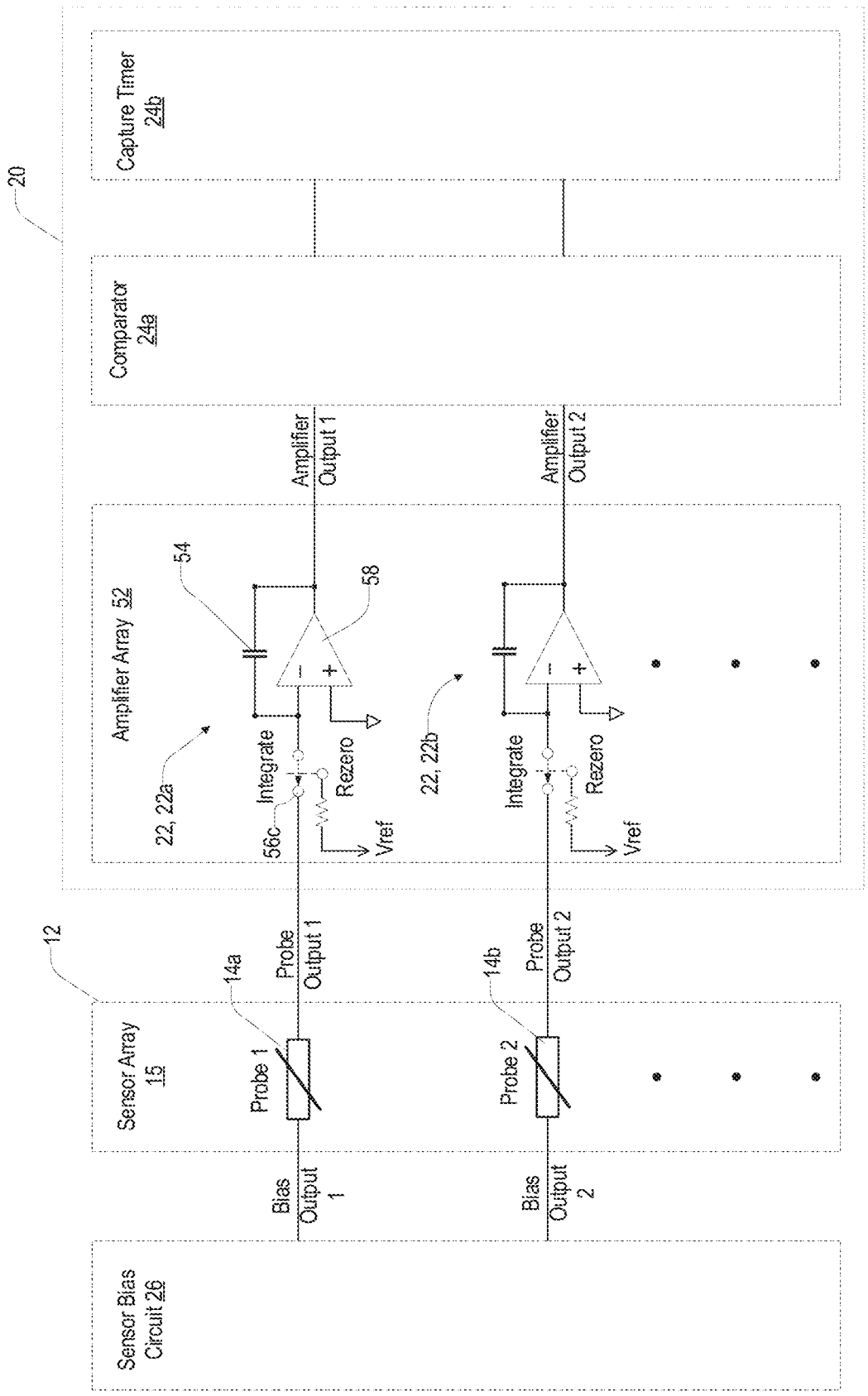
FIG. 4B is a schematic diagram of a chemical sensor array comprising a readout circuit configured to monitor voltage via a dual-slope A/D conversion.

In some implementations as exemplified in FIG. 4B, the readout circuit 24 may be implemented with a zero-crossing detector 24a and a capture timer 24b. The "zero" point may have a magnitude greater than zero in a unipolar power supply implementation. As shown, the integration block is modified, such that the controller 10 can select either the unknown current or a reference current of opposite polarity to the unknown. In operation, the unknown is integrated for a known time period. The reference is then integrated until the output of the integrator reaches the zero level. The capture timer 24b measures this re-zero time. This re-zero time is directly proportional to the unknown current. This measurement method may be referred to as dual-slope A/D conversion and is capable of very high resolution. The capture timer 24b may be implemented in a microprocessor peripheral or other digital hardware. Dual-slope A/D conversion is less complex and low cost than many other A/D conversion methods, but also tends to have a slow conversion rate. For some applications, this combination of high, resolution, low-cost, and slow conversion may be beneficial.

In addition to the sensitive nature of the signals output from the sensors 14, the operation of each of the sensors 14a, 14b, 14b, etc. may be dependent on the input signal supplied to the sensors 14. Accordingly, the system 8 may further comprise a sensor bias circuit 26. The sensor bias circuit 26 may comprise one or more circuits configured to supply a voltage to each of the sensors 14a, 14b, 14c, etc. in response to a control signal from the controller 10. For example, the sensor bias circuit 26 may comprise a plurality of converters (e.g., digital-to-analog converters [DAC]) configured to generate input signals supplied to each of the sensors 14a, 14b, 14c, etc. In this configuration, the controller 10 may be configured to supply independent control signals to each of the sensors 14a, 14b, 14c, etc. The independent control signals may differ in timing, voltage, frequency, and other characteristics that may support the operation of each of the sensors 14a, 14b, 14b, etc. of the array 15 to accurately respond to the presence of chemicals proximate to the array 15.

Though discussed in reference to specific sensors (e.g. nanofiber chemical sensors), the chemical detection device 12 may comprise a variety of sensory devices. For example, the chemical detection device 12 may be implemented by a variety of devices including, but not limited to, electrochemical sensors, amperometric gas sensors, carbon monoxide sensors, catalytic bead sensors, thermal conductivity sensors, metal oxide sensors (MOS), infrared (IR) sensors, photoionization detectors (PID), etc. Such sensors may vary in application and, therefore, may be implemented in various combinations to achieve the identification and detection of various chemicals and contaminants that may be present proximate to the detection device 12. Though specific examples are discussed herein, the chemical detection device 12 may be implemented by similar sensors or developing sensory technologies without departing from the spirit of the disclosure.

As discussed herein, the controller 10 may comprise one or more processors or microcontrollers, a field-programmable gate array (FPGA), application-specific integrated circuit (ASIC), or other processing devices depending on the application. For example, if the sensors 14 of the device 12 are not very numerous, a simple processing unit may be sufficient to enable basic detection via the associated sensors 14. However, if the sensors 14 are more numerous and the corresponding control structure requires more concurrent or programmable operations, the FPGA may be better suited to provide for the operation of the controller 10 as discussed herein. As discussed in reference to FIGS. 2 and 3, the detection device 12 may be configured for more than one sensor, which may suggest the necessity for a complicated control structure. As discussed herein, such a control structure may include an independent supply of bias voltage via the sensor bias circuit 26 as well as independent readout timing control and readout of the charges associated with each of the sensors 14a, 14, 14c, etc. In some implementations, the sensor bias circuit 26 may also include bias resistors, such that a negative or positive signal may be supplied to each of the sensors 14.

In some embodiments, the controller 10 may further be in communication with one or more communication circuits 30 configured to communicate with one or more external devices, computers, and/or user interfaces. In some embodiments, the communication circuit 30 may correspond to a wired connection (e.g., Universal Serial Bus (USB), Thunderbolt, External Serial Advanced Technology Attachment (eSATA), etc. Additionally, the controller may comprise a wireless network interface. As discussed herein, wireless communication protocols may operate in accordance with communication standards including, but not limited to, ground air cellular towers, global system for mobile communications (GSM), code division multiple access (CDMA), Long Term Evolution (LTE or 4G LTE), etc.; satellite-based communications; and/or variations thereof. Accordingly, the controller 10 of the system 8 may be configured to send alerts or signals to various devices configured to communicate via one or more wired or wireless communication protocols.

Figure 2:
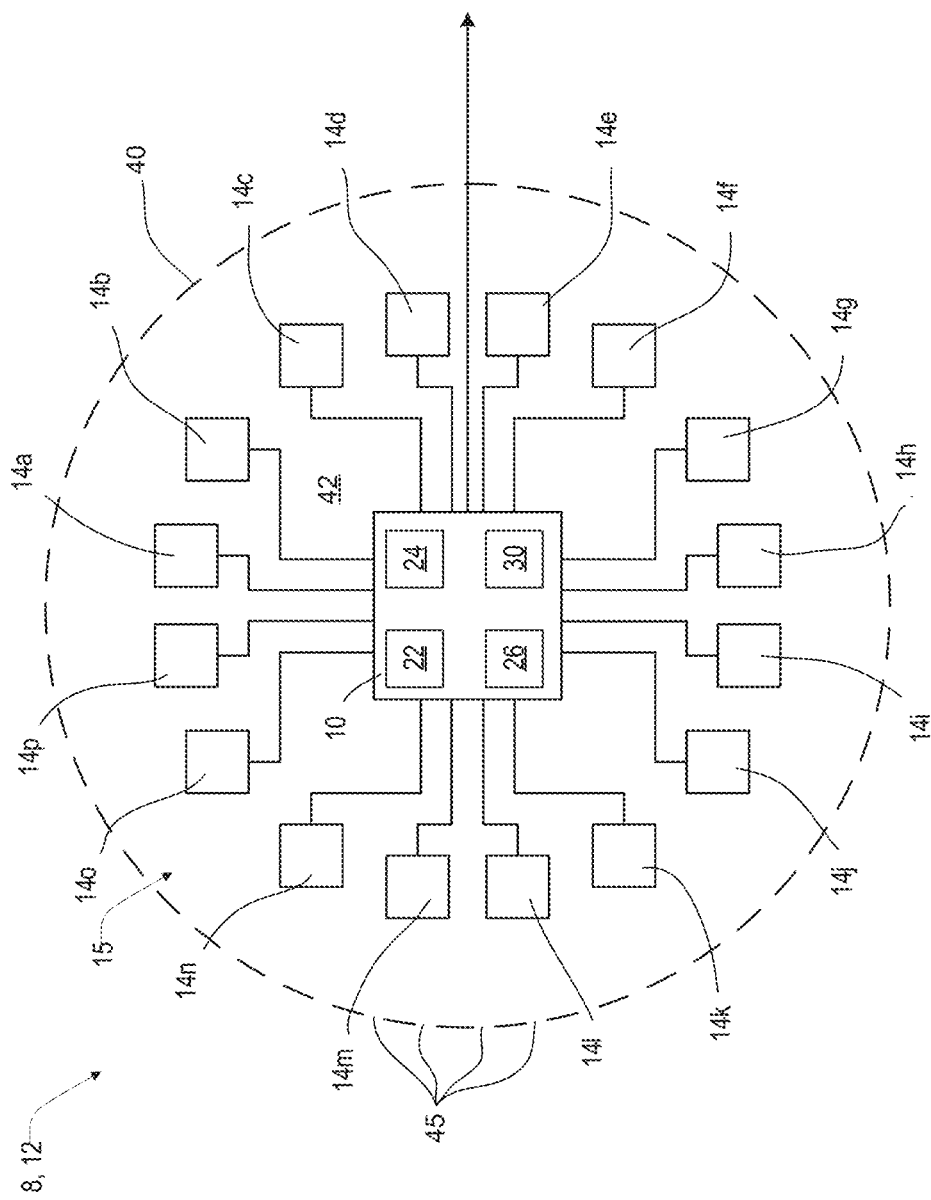
FIG. 2 is an electrical circuit diagram of a chemical detector.
Figure 3:
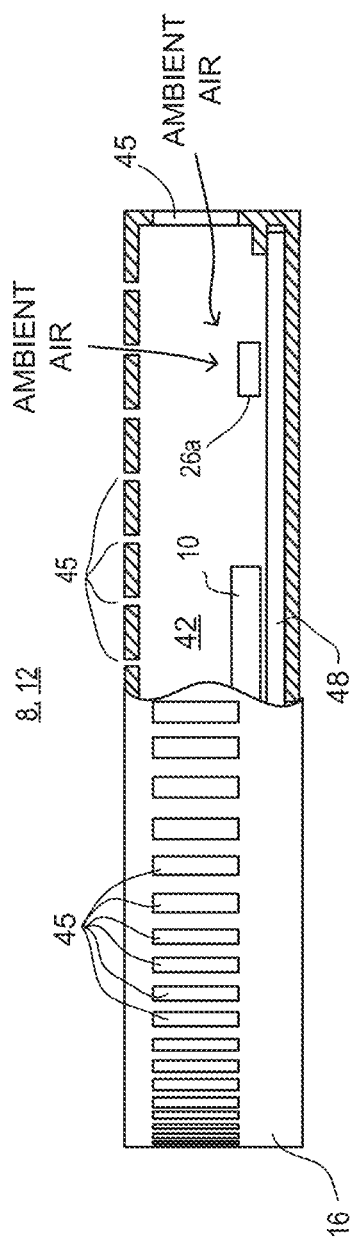
FIG. 3 is a side schematic view of the chemical detection device shown in partial cross-section.

Referring now to FIGS. 2 and 3, an example of the detection device 12 is shown in communication with at least one of the nanofiber chemical sensors 14. The nanofiber chemical sensor 14 may be configured to sense various chemicals and compounds that may be present in the ambient air proximate to the housing 16. In some embodiments, the at least one nanofiber chemical sensor 14 may comprise a plurality of nanofiber chemical sensors 14a-14p. Though identified in this particular example to include sixteen sensors 14, the number of sensors 14 may vary and be adjusted to suit a desired application. In operation, each of the one or more nanofiber chemical sensors 14 may be in communication with the controller 10, which may be configured to monitor changes in electrical characteristics for each of the nanofiber sensors 14 in the presence of the various airborne materials. Based on the combination of signals received from chemical sensors 14, the controller 10 may be configured to identify the presence of one or more contaminants proximate to the detection device 12.

The nanofibers used in the sensors 14 may be synthesized with specific functional groups that can interact with airborne materials/vapors/particles. The nanofibers are deposited on an interdigitated electrode to form an electrode-nanofiber array. Interaction of the nanofibers with airborne materials changes the measured electrical characteristics of the nanofiber chemical sensor. An increase or decrease in the measured current or effective resistance of each of the nanofiber chemical sensors occurs as a result of these airborne material interactions.

Nanofibers of each of the sensors 14 with different functional groups have a different response to the same airborne material. By using the plurality of nanofiber chemical sensors 14 in the array 15, an identifying response signature can be established by the controller 10 for each of a plurality of airborne materials. Accordingly, based on the electrical signals communicated from the array 15, the controller 10 may be configured to detect a variety of conditions that may exist proximate to the sensor array 15. The nanofibers of the sensors 14 may have a proportionately large three-dimensional surface area that is resistant to particulate fouling. In various embodiments, the controller 10 may be configured to identify a variety of contaminants. In response to the particular contaminant or family of contaminants identified by the detection device 12, the system 8 may be configured to respond by outputting information that may assist in the detection or correction of a condition related to the detection.

In various embodiments, the detection device 12 may be configured to identify a variety of chemicals present in a detection zone or region. Chemicals and compounds that may be detected by the system 8 may be trained or programmed based on electrical signatures received by the controller 10 in response to the presence of the chemicals. Examples of chemicals that may be identified and/or detected may include, but are not limited to, Benzaldehyde, Hexane, Acetone, Ethanol, Diesel Fuel, Nitrobenzene, and Formaldehyde. Some examples of explosives and chemical agents that may be detected may include Nitromethane, DNT (Dinitrotoluene), TNT (Trinitrotoluene), ANFO (Ammonium Nitrate Fuel Oil), Ammonium Nitrate, PETN (may detect taggant), RDX (may detect taggant), TATP (Triacetone Triperoxide), H2O2 (Hydrogen Peroxide), TEP (Triethylphosphate), DMMP (Dimethyl methylphosphonate), 2-Chloroethyl ethyl sulfide, Triphosgene, and Methyl Salicylate. Some examples of toxic chemicals that may be detected by the detection device 12 include, but are not limited to, Chlorine Gas, Ammonia, Hydrogen Peroxide, Sulfur Dioxide, Hydrochloric Acid, TEP (Triethyl Phosphate), Phosphine, Hydrogen Cyanide, Arsine, and Formaldehyde. In some examples, the detection device may also be configured to detect one or more chemicals commonly found in consumer foods and/or goods including, but not limited to, Trichloroanisole, Melamine, Trimethylamine, Limonene, Pinene, Linalyl acetate, Menthol, Menthone, and Linalool. The device 12 may additionally be configured to detect various amines including, but not limited to, N-Methylphenethylam-lamine, Phenethylamine, Methylamine, Aniline, Triethylamine, and Diethylamine. Accordingly, based on the detection of each of the chemicals detected by the controller 10, a signal or information may be communicated via the communication circuit 30 to indicate the chemical presence.

Referring now to FIG. 3, the chemical sensors 14a-14p of the detection device 12 may be arranged in any manner and may be disposed in an inner chamber 42 of the housing 16 having a plurality of air vents 45. The air vents 45 may provide for ambient and/or forced air to flow into the inner chamber 42. In this configuration, updated air samples flow past the chemical sensors 14a-14p providing consistently updated monitoring of the chemical particulates present in the air. In various implementations, the air vents 45 may be large enough and/or numerous enough to allow the ambient air to flow into the inner chamber 42 without restriction. The controller 10 may be in communication with various systems and/or controllers that may be associated with additional devices and/or interfaces via the communication circuit 30. In various implementations, the communication circuit 30 may correspond to a wired and/or wireless connection. Accordingly, the system 8 may be configured to communicate one or more warnings, instructions, and/or additional information to a user, device, or remote server in response to the detection of one or more chemicals via the detection device 12.

Common chemicals and corresponding odors that may be detected by the device 12 may vary widely. For example, the device 12 may be configured to identify a variety of odors including, but not limited to, perfumes, feces, fish, skunk, pet odor, decaying biological material, methane, hydrogen sulfide, body odor (body-related bacterial odor), smoke, alcohol, bodily fluids, vomit, etc. Some of these odors may relate to comfort issues while others could present health issues or security concerns to those exposed. Accordingly, the system 8 may additionally communicate a concentration of the chemicals detected by the device 12 via the communication circuit 30 of the controller 10.

Additionally, the detection device 12 may be configured to detect and identify a variety of chemicals that may generally be considered dangerous, which may or may not cause a significant odor. Examples of such chemicals or sources of such chemicals may be allergens including, but not limited to, peanuts, soy, perfumes, smog, etc. Additional examples of chemicals or sources of such chemicals may include, but are not limited to, explosives, gun powder, accelerants, carbon dioxide, carbon monoxide, volatile organic compounds (VOCs), drugs (e.g. methamphetamine, alcohol), smog, smoke, exhaust, etc. In response to the detection of such chemicals, the system 8 may respond in different ways, particularly in comparison to the detection of chemicals that may not be dangerous to users or individuals in the area of the detection device 12.

Referring now to FIG. 4A, a diagram of the sensor array 15 is shown in conductive communication with the sensor bias circuit 26. As previously described, the sensor bias circuit 26 may be configured to supply an analog voltage to each of the sensors 14a, 14b, 14c, etc. in response to a control signal from the controller 10. For example, the sensor bias circuit 26 may comprise a plurality of digital-to-analog converters (DACs) configured to generate voltages ranging from approximately ±15V in response to digital input signals supplied by the controller 10. In this configuration, the controller 10 may be configured to supply independent control signals to control the bias voltage delivered to each of the sensors 14a, 14b, 14c, etc. Additionally, the controller 10 may supply each of the sensors 14a, 14b, 14c, etc. with the bias voltage or control signal at different times and frequencies depending on the desired operation of each of the sensors 14a, 14b, 14c, etc. for an application and other characteristics that may support the operation of each of the sensors 14a, 14b, 14b, etc. of the array 15 to accurately detect the chemicals proximate to the array 15.

As depicted, the sensors 14 of the sensor array 15 may correspond to chemiresistors, which are shown modeled as variable resistors. The sensors 14 may be formed of nanofibers disposed between interdigitated fingers of electrode pairs. The nanofibers may form a porous structure across the electrode pairs configured to capture targeted molecules in the air proximate to the detection device 12. When the nanofibers come in contact with target analytes or chemicals, a change in the electrochemical characteristics of the nanofibers may occur. The change in electrochemical characteristics may result in increases or decreases in the signal output to the amplifier circuit 22. An input side of the electrode pair may be connected to the sensor bias circuit 26, and an output side of the electrode pair may be connected to the amplifier circuit 22 (e.g., 22a, 22b, etc.). As shown, the amplifier circuits 22 connected to the sensors 14 may form an amplifier array 52.

In operation, the controller 10 may be configured to control an exposure of each of the sensors 14a, 14b, etc. to a light source (not shown). The light source may induce photocurrent across the nanostructure, which may reduce the resistance of the nanofiber structure between the electrode pair as well as increase the reactive nature of the nanofibers to chemicals coming in contact with the nanofibers. In this configuration, the current passing through each of the sensors 14a, 14b, etc. may vary independently in response to the exposure of different chemical structures that contact or are captured in the porous structures of the different sensors 14 of the sensor array 15. The small changes in current may be accumulated over exposure times by a capacitor 54 of each of the amplifier circuits 22a, 22b, etc. Once the exposure time has elapsed, the controller 10 may control a first switch 56a. The first switch 56a may be configured to cause the accumulated charge to be held in the capacitor 54, such that the corresponding charge may be read out by the readout circuit 24 (e.g. an analog-to-digital converter [ADC]) and communicated to the controller 10 from an op-amp 58 of the amplifier circuit 22.

Once the charge is read out from the amplifier circuit 22, the controller 10 may be configured to control a second switch 56b to reset or discharge the capacitor 54, such that the accumulation of the current may again be measured over an integration period. In this way, the accumulated charges of each of the sensors 14 of the array 15 may be monitored and processed by the controller 10 and/or additional computers or controllers to determine variations in resistance in the resistance of the sensors 14. Based on the variations in the resistances of the sensors 14 and the corresponding changes in the charges accumulated in the capacitors, the controller 10 may determine or infer the chemical compositions or types of materials to which the detection device 12 is exposed. As discussed herein, the controller 10 may be configured to independently adjust the duration and timing (e.g. frequency) of the integration period of each of the sensors 14. Additionally, the controller 10 may adjust the integration periods of the amplifier circuits 22 over time in order to ensure that the accumulated charges are sufficient to measure and limited to avoid saturation of the capacity of the capacitor 54. In this way, the controller 10 may monitor and compute the changes in the resistance of each of the sensors 14.

As depicted in FIG. 4A, the amplifier circuits 22 each comprise the op-amp 58 conductively connected to the bias output at an inverting input. The first switch 56a (e.g. a hold switch) may be disposed between the bias output and the inverting input allowing the controller 10 to selectively disconnect the bias output from the amplifier circuit 22. The non-inverting input of the op-amp 58 may be connected to the ground, and the output may be in connection with the readout circuit 24. The second switch 56b (e.g. a reset switch) and the capacitor 54 may be connected in parallel from the inverting input to the output of the op-amp 58. In this configuration, each of the amplifier circuits 22a, 22b, etc. may be configured to integrate a charge supplied by each of the sensors 14a, 14b, etc. and supply a charge value to the readout circuit 24. The charge value is representative of a resistance of each of the sensors 14a, 14b, etc. and may be calculated based on the known voltage supplied to the sensors 14 over the integration period or a time interval, which is also controlled by and known by the controller 10. In this way, the resistance of each of the sensors 14a, 14b, etc. at a sample time may be identified by the controller 10 to infer or calculate a concentration of a chemical compound proximate to the detection device 12 while filtering transient spikes and noise that may otherwise cause significant error.

The chemical composition of the airborne material detected by the sensors 14a, 14b, etc. may be distinguished from a plurality of chemical compositions based on a combination of the resistances identified for the sensors 14a, 14b, etc. Such combinations of resistances may correspond to representative resistance characteristics or resistance signatures that are compared by the controller 10 to a table or library of resistance characteristics for various chemical compositions. In this way, the controller may compare the detected resistances to the resistance characteristics to identify the specific chemical composition and distinguish the composition from various chemical compositions that may be identified by the system 8. In other words, the system 8 may monitor and compare the resistances of the sensors 14a, 14b, etc. and compare the resistances to corresponding combinations of resistance values of the sensors 14a, 14b, etc. that correlate to the presence of specific chemical compositions or families of chemicals. Accordingly, by monitoring the resistances of the sensors 14a, 14b, etc., the system 8 may determine or detect the presence of various chemical compositions based on the resistances of the sensors 14a, 14b, etc. as indicated by the characteristic response of the sensors 14a, 14b, etc. to the chemical composition.

Referring now to FIG. 4B, the readout circuit 24 may be implemented with a zero-crossing detector 24a (e.g. comparator) and a capture timer 24b. As shown, the integration block is modified such that the controller 10 can select either the unknown current or a reference current of opposite polarity to the unknown via a three-way switch, which may be referred to as an integration switch 56c. The integration switch 56c is in connection with the inverting input of the op-amp 58. In operation, the unknown current is integrated for a known time period. The reference is then integrated until the output of the integrator reaches the zero level. The capture timer 24b measures this re-zero time. This re-zero time is directly proportional to the unknown current.

Figure 5:
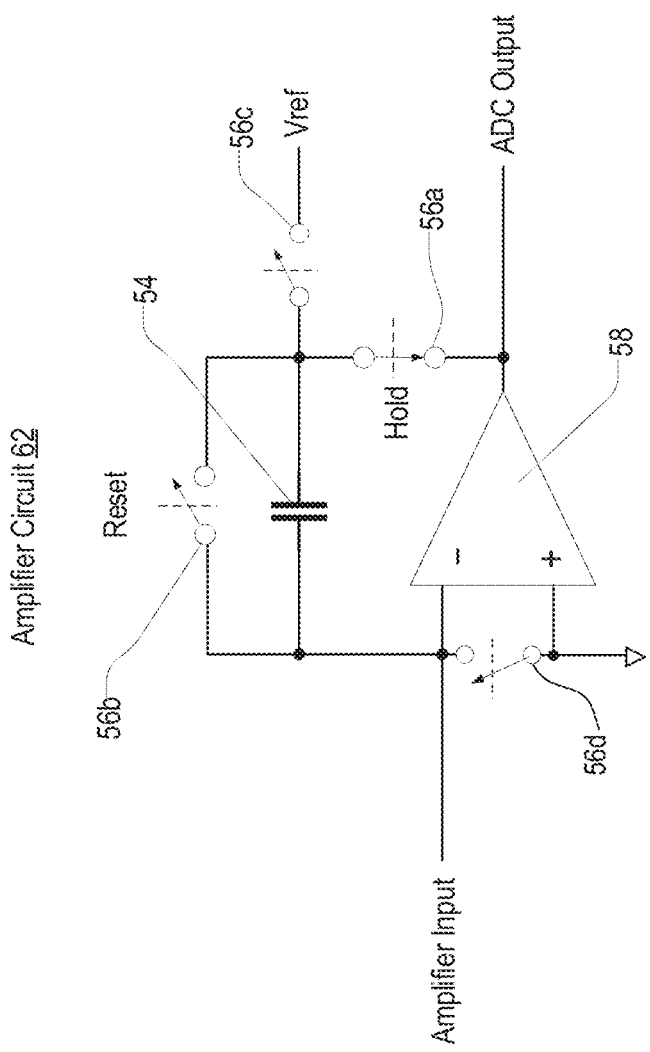
FIG. 5 is a circuit diagram of an amplifier circuit for a chemical sensor.

Referring now to FIG. 5, a circuit diagram of an amplifier circuit 62 as discussed herein is shown. The amplifier circuit 62 may be similar to the amplifier circuit 22 and accordingly, the description of the amplifier circuit 62 may focus on the aspects that may differ, and like reference numerals may be used to refer to like parts. The amplifier circuit 62 may comprise the op-amp 58 conductively connecting the bias output to an inverting input of the op-amp 58. The non-inverting input of the op-amp 58 may be connected to a ground. The second switch 56b (e.g. a reset switch) and the capacitor 54 may be connected in parallel from the inverting input to the output of the op-amp 58. The first switch 56a may be connected in series between the output of the op-amp 58 and the parallel connection of the capacitor 54 with the second switch 56b.

Additionally, a third switch 56c may be configured to selectively connect the capacitor 54 to a reference voltage Vref. The third switch 56c may also be controlled by the controller 10 and may be connected in series between an input of the reference voltage Vref and the parallel connection of the capacitor 54 with the second switch 56b. Finally, the amplifier circuit 62 may further comprise a charging switch 56d connected from the inverting input of the op-amp 58 to the ground. The operation of the charging switch 56d may also be controlled by the controller 10 and provide for the control of the charging of the capacitor 54. Accordingly, the disclosure may implement the amplifier circuit 62 to monitor a charge generated by the at least one sensor over a time interval as provided by the disclosure.

Figure 6:
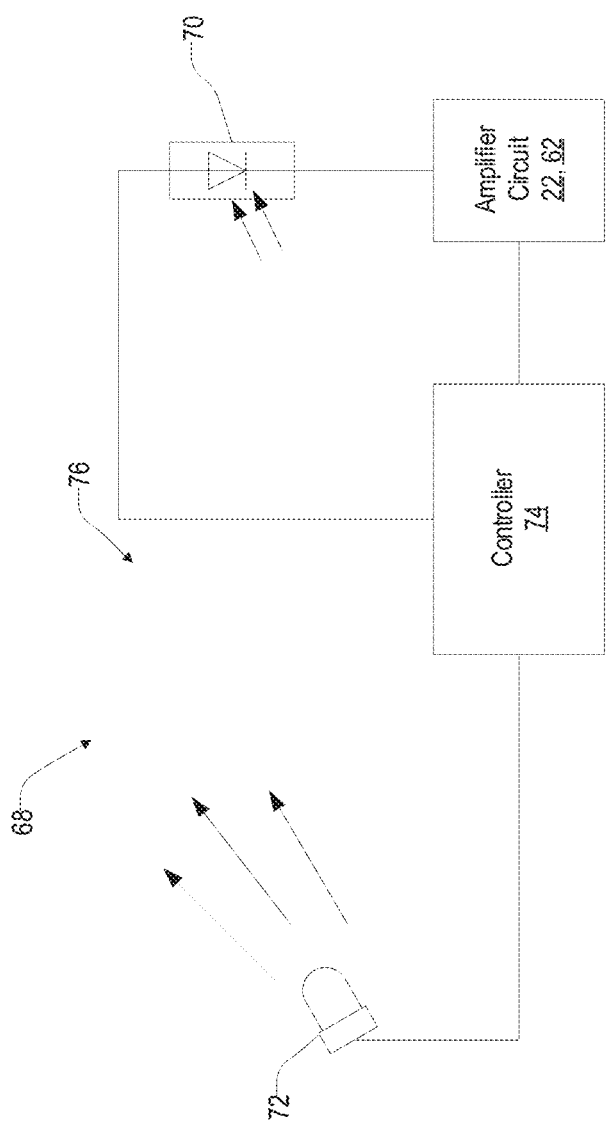
FIG. 6 demonstrates a schematic diagram of a light sensor in accordance with the disclosure.

Referring now to FIG. 6, a schematic diagram of a light detection system 68 is shown demonstrating a photosensor 70 (e.g. a photodiode) configured to monitor a light transmitted from an emitter 72 (e.g. a light-emitting diode [LED], halogen bulb, xenon bulb, etc.). Though discussed in reference to the emitter 72, the photosensor 70 may similarly be applied to monitor an environmental light source or daylight condition. In operation, a controller 74 may be configured to activate the emitter 72 and monitor the light received by the photosensor 70. Similar to the sensors 14 of the detection device 12, the photosensor 70 may vary in output current in response to a local environment. The photosensor 70 may react by varying in photocurrent output to the amplifier circuit 22, 62 based on changes in light impinging upon the photosensor 70. In this way, the controller 74 may detect fluctuations in the light received by the photosensor 70 from the emitter 72. In some implementations, the controller 74 may infer or determine the presence of a particle in an open region 76 between the emitter 72 and the photosensor 70 and make inferences as to the quality, condition, and/or transmittance or transparency of air in the open region 76. Similarly, the controller 74 may be configured to determine a brightness or relative luminance of a local environment in instances where the emitter 72 is not controlled by the controller 74 and instead corresponds to an environmental light source or external light source (e.g. the sun, streetlights, etc.). Accordingly, the disclosure provides for a flexible solution that may be implemented in a variety of beneficial implementations.

As discussed herein the light detection system may correspond to a smoke or particulate sensor as discussed in U.S. Pat. No. 6,876,305, entitled "COMPACT PARTICLE SENSOR," U.S. Pat. No. 6,653,942, entitled "SMOKE DETECTOR," U.S. Pat. No. 6,326,897, entitled "SMOKE DETECTOR," and U.S. Pat. No. 6,225,910, entitled "SMOKE DETECTOR," the entire disclosures of which are hereby incorporated herein by reference.

It will be understood by one having ordinary skill in the art that construction of the described device and other components may not be limited to any specific material. Other exemplary embodiments of the device disclosed herein may be formed from a wide variety of materials unless described otherwise herein.

For purposes of this disclosure, the term "coupled" (in all of its forms, couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent or may be removable or releasable unless otherwise stated.

It is also important to note that the construction and arrangement of the elements of the device as shown in the exemplary embodiments is illustrative only. Although only a few embodiments of the present innovations have been described in detail in this disclosure, those skilled in the art who review this disclosure will readily appreciate that many modifications are possible (e.g., variations in sizes, dimensions, structures, shapes, and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements shown as multiple parts may be integrally formed, the operation of the interfaces may be reversed or otherwise varied, the length or width of the structures and/or members or connector or other elements of the system may be varied, the nature or number of adjustment positions provided between the elements may be varied. It should be noted that the elements and/or assemblies of the system may be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary embodiments without departing from the spirit of the present innovations.

It will be understood that any described processes or steps within described processes may be combined with other disclosed processes or steps to form structures within the scope of the present device. The exemplary structures and processes disclosed herein are for illustrative purposes and are not to be construed as limiting.

It is also to be understood that variations and modifications can be made on the aforementioned structure without departing from the concepts of the present invention, and further it is to be understood that such concepts are intended to be covered by the following claims unless these claims by their language expressly state otherwise.

The above description is considered that of the illustrated embodiments only. Modifications of the device will occur to those skilled in the art and to those who make or use the device. Therefore, it is understood that the embodiments shown in the drawings and described above are merely for illustrative purposes and not intended to limit the scope of the device, which is defined by the following claims as interpreted according to the principles of patent law, including the Doctrine of Equivalents.

What is claimed is:

1. A detection system comprising:
    at least one sensor configured to measure a presence of airborne particles, wherein the at least one sensor comprises a variable resistance that varies in response to a concentration of a chemical composition of the airborne particles;
    at least one amplifier circuit in communication with the at least one sensor, wherein the amplifier circuit is configured to monitor a charge generated by the at least one sensor over a time interval; and
    a controller configured to:
        monitor the charge accumulated in the at least one amplifier circuit from the at least one sensor at the time interval;
        in response to the charge of the at least one amplifier circuit, detect the presence of the airborne particles; and
        detect the concentration of the chemical composition in response to identifying changes in the variable resistance, wherein the changes in the variable resistance are determined based on the charge of the at least one amplifier circuit and a voltage potential of a bias voltage supplied to the at least one sensor.

2. The system according to claim 1, further comprising a light source wherein the at least one sensor is configured to detect light emitted from the light source.

3. The system according to claim 1, wherein the at least one sensor comprises a nanofiber chemical sensor for sensing the chemical composition of the airborne particles.

4. The system according to claim 1, wherein the at least one amplifier circuit comprises an op-amp conductively connected to a sensor output from the at least one sensor, wherein a capacitor and a switch are connected to the sensor output from the at least one sensor in parallel with the op-amp.

5. The system according to claim 4, wherein the sensor output is in connection with an inverting input of the op-amp.

6. The system according to claim 1, wherein the at least one sensor comprises a plurality of nanofiber chemical sensors, and further comprising:
    a bias circuit configured to supply a plurality of bias voltages to each of the plurality of nanofiber chemical sensors.

7. The system according to claim 6, wherein the controller is further configured to:
    control the bias circuit to supply the plurality of bias voltages as different voltages to each of the plurality of chemical sensors.

8. The system according to claim 6, wherein the bias circuit comprises a plurality of digital-to-analog converters configured to supply the plurality of bias voltages as different voltages to the plurality of chemical sensors in response to control signals supplied from the controller.

9. The system according to claim 6, wherein the at least one amplifier circuit comprises a plurality of amplifier circuits in connection with each of the chemical sensors, wherein the controller is further configured to:
    monitor the charge accumulated in the amplifier circuits from the at least one sensor at the time interval; and
    determine the resistance of each of the chemical sensors based on the charge of the amplifier circuits and voltage values of the plurality of bias voltages.

10. The system according to claim 9, wherein the controller is further configured to:
    detect a concentration of the chemical composition of the airborne particles based on the determined resistance of one or more of the chemical sensors.

11. The system according to claim 9, wherein the controller is further configured to:
    independently control the time interval for an integration period for each of the plurality of amplifier circuits, thereby independently controlling the integration period for each of the chemical sensors in connection with the corresponding amplifier circuits.

12. The system according to claim 11, wherein the controller is further configured to:
    distinguish the chemical composition of the airborne particles among a plurality of chemical compositions in response to combinations of the resistances of the chemical sensors.

13. A method for detecting a presence of airborne particles comprising:
    supplying a plurality of bias voltages to a plurality of chemical sensors;
    receiving and accumulating current from each of the chemical sensors with a corresponding amplifier circuit;
    monitoring charges accumulated in the amplifier circuits from each of the chemical sensors over a plurality of corresponding accumulation periods;

determining the resistance of each of the chemical sensors based on the charge of the amplifier circuits and voltage values of the plurality of bias voltages; and identifying the presence of the airborne particles based on the resistances determined for the chemical sensors.

14. The method according to claim 13, wherein the voltage potential of the bias voltages supplied to the chemical sensors is independently controlled by converting control signals from a controller to the bias voltages.

15. The method according to claim 14, wherein the chemical composition of the airborne particles is further identified based on the resistances determined for the chemical sensors.

16. The method according to claim 13, wherein the monitoring of the charges accumulated in the amplifier circuits from each of the chemical sensors comprises controlling an integration period for the accumulation of the charges.

17. The method according to claim 16, wherein the integration period for each of the amplifier circuits is independently controlled, such that each of the integration periods may vary a duration over which the charges are accumulated by each of the amplifier circuits.

18. A chemical detection system comprising:
a plurality of chemical sensors configured to vary in resistance in response to a presence of airborne particles;
a bias circuit configured to supply bias voltages to each of the chemical sensors;
a plurality of amplifier circuits in communication with the chemical sensors; and
a controller configured to:
control the bias circuit to supply the plurality of bias voltages to each of the plurality of chemical sensors;
monitor charges accumulated in the amplifier circuits from the chemical sensors over a corresponding integration period in response to the bias voltages;
determine the resistance of the chemical sensors based on the charges accumulated in the amplifier circuits and voltage values of the plurality of bias voltages; and
detect a chemical composition of the airborne particles based on the determined resistances of the chemical sensors.

\* \* \* \* \*